United States Patent [19]

Cordi et al.

[11] Patent Number: 5,776,949
[45] Date of Patent: Jul. 7, 1998

[54] 2-(1H) QUINOLINONE COMPOUNDS

[75] Inventors: Alex Cordi, Suresnes; Patrice Desos, Courbevoie; Jean Lepagnol, Chaudon; Philippe Morain, Issy les Moulineaux; Pierre Lestage, La Celle Saint Cloud, all of France

[73] Assignee: Adir et Compagnie, Courbevoie, France

[21] Appl. No.: 889,920

[22] Filed: Jul. 10, 1997

[51] Int. Cl.⁶ .......................... A61K 31/47; C07D 215/36
[52] U.S. Cl. ................................. 514/312; 546/155
[58] Field of Search ............................ 546/155; 514/312

[56] References Cited

PUBLICATIONS

Sterescu et al., "Determination of aminopyrine in antigermine", Revista de Chimie, vol. 12, p. 233 1961.
Frenkel, Chemical Abstracts, vol. 56, No. 11, 13012d 1962.

Primary Examiner—Emily Bernhardt
Assistant Examiner—Ann M. Kessinger
Attorney, Agent, or Firm—The Firm of Gordon W. Hueschen

[57] ABSTRACT

A compound of formula (I):

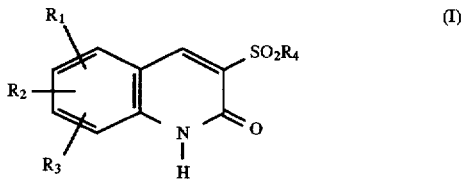

in which:

$R_1$, $R_2$, $R_3$, which are identical or different, represent hydrogen, halogen, alkyl, nitro, cyano, aminosulfonyl, imidazolyl, or pyrrolyl, or alternatively, when two of them are situated on adjacent carbons, may form with the carbon atoms to which they are attached a benzene ring on $C_3$–$C_7$ cyloalkyl $R_4$ represents hydroxyl, alkoxy, phenoxy, or amino, their isomers as well as their addition salts with a pharmaceutically-acceptable base, and medicinal products containing the same which are useful as inhibitors of the the pathological phenomena linked to hyperactivation of the neurotransmission pathways by the excitatory amino acids.

8 Claims, No Drawings

2-(1H) QUINOLINONE COMPOUNDS

The present invention relates to new 2-(1H)-quinolinone compounds.

BACKGROUND OF THE INVENTION

Some 2-(1H)-quinolinone derivatives have been described in the literature. This is the case, for example, for the compounds described by C. ALABASTER et al. (J. Med. Chem., 31, 2048–2056, 1988) which are cardiac stimulants or those described by F. BAHR et al. (Pharmazie, 36, H.10, 1981).

DESCRIPTION OF THE INVENTION

The compounds described in the present invention, in addition to the fact that they are new, have particularly advantageous pharmacological properties: they are potent inhibitors of phenomena linked to neuronal hyperactivation caused by excitatory amino acids.

L-Glutamic acid and L-aspartic acid have the capacity to activate the neurons of the central nervous system and numerous studies have demonstrated that these excitatory amino acids (EAA) meet the criteria which define a neurotransmitter. Accordingly, the modulation of the neuronal events linked to these EAAs appears to be an advantageous target for the treatment of neurological diseases.

Indeed, it has been proved that the excessive liberation of EAAs and the hyperstimulation of their receptors might be one of the causes of the neuronal degeneration which is observed in epilepsy, senile dementia or cerebral vascular accidents. Currently, the number of neurodegenerative diseases in which the EAAs are closly implicated is constantly rising (Huntington's chorea, schizophrenia, lateral amyotrophic sclerosis) (Mc GEER E. G. et al., Nature, 263, 517–519, 1976; SIMON R. et al., Science, 226, 850–852, 1984).

Furthermore, while it is certain that the hyperactivation of neurotransmission by the EAAs exerts neurotoxic effects, its normal activation facilitates memory and cognitive performances (LYNCH G. & BAUDRY M., Science, 224, 1057–1063, 1984; ROTHMAN S. M. & OLNEY J. W., Trends in Neuro Sci., 10, 299–302, 1987). From the pharmacological and therapeutic point of view, it is therefore appropriate to prevent only pathological stimulations while observing the physiological activation level.

The EAA receptors of post- and presynaptic location have been classified into 4 groups according to the affinity and the electrophysiological and/or neurochemical effects of specific ligands: NMDA (N-méthyl-D-aspartate) receptor associated with an ion channel which is permeable to mono- and divalent cations (including calcium) but which is blocked by magnesium. The accumulation of calcium and zinc in the cell is thought to be one of the causes of neuronal death. The opening of the NMDA channel is regulated by several sites associated with the receptor and in particular is enhanced by glycine whose effect is strychnine-insensitive. This glycine site constitutes one of the major targets for modulating the activation of the NMDA receptor.

AMPA ((α-amino-3-hydroxy-5-methyl-4-isoxazole-propionic acid) receptor associated with an ion channel which is permeable to the monovalent cations including sodium. The activation of this channel is thought to lead to membrane depolarization.

kainate receptor whose ionic characteristics are similar to those of the AMPA receptor but which differs from it in the levels of conductance and desensitization. However, numerous studies tend to prove that the AMPA receptor and the kainate receptor have close structural and functional analogies and constitute one receptor family (KEINANEN K. et al., Science, 249, 556–560, 1990).

ACPD (trans-1-aminocyclopentane-1,3-dicarboxylic acid) receptor, called metabotropic receptor because it is not coupled to an ion channel.

The activation of the ionotropic receptors by the EAAs opens the ion channels and in particular allows the entry of sodium which depolarizes the cell. This first phase, which involves the AMPA receptor, then leads to the deinhibition and then to the hyperactivation of the NMDA receptor and to the massive accumulation of calcium (BLAKE J. F. et al., Neurosci. Letters, 89, 182–186, 1988; BASHIR Z. I. et al., Nature, 349, 156–158, 1991).

The compounds of the present invention or the products of their metabolic hydrolysis (prodrugs) are therefore intended, in a novel fashion, to prevent the excitatory and toxic effects of the EAAs by blocking the initial activation of the AMPA/kainate receptor. The compounds of the present invention are therefore useful as inhibitors of the pathological, especially neurotoxic, phenomena linked to the hyperactivation of the neurotransmission pathways by the excitatory amino acids. They differ from the products described in European patent application EP 542609 in that they are particularly soluble in water, are completely free of color and have good cerebral bioavailability after systemic administration.

They are therefore potential therapeutic agents for the treatment of neurological and psychological diseases involving these amino acids: acute or chronic degenerative diseases such as cerebral vascular accident, cerebral or spinal trauma, epilepsy, chronic neurodegenerative diseases such as Alzheimer's disease, schizophrenia, lateral amyotrophic sclerosis or Huntington's chorea.

More specifically, the invention relates to the compounds of formula (I):

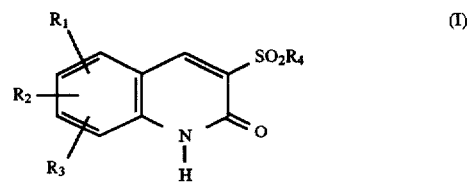

in which:

$R_1$, $R_2$, $R_3$, which are identical or different, represent a hydrogen atom, a halogen atom, a linear or branched ($C_1$–$C_6$) alkyl group (substituted or otherwise with one or more halogen atoms), a nitro group, a cyano group, an aminosulfonyl group, an imidazolyl group (substituted or otherwise with one or more linear or branched ($C_1$–$C_6$) alkyl or linear or branched amino ($C_1$–$C_6$) alkyl groups) or a pyrrolyl group (substituted or otherwise with one or more linear or branched ($C_1$–$C_6$) alkyl or linear or branched amino($C_1$–$C_6$) alkyl groups), or alternatively, when two of them are situated on adjacent carbons, form with the carbon atoms to which they are attached a benzene ring (substituted or otherwise with one or more halogen atoms, linear or branched ($C_1$–$C_6$) alkyl, linear or branched ($C_1$–$C_6$) alkoxy or trihalomethyl groups) or a ($C_3$–$C_7$) cycloalkyl ring in which a —$CH_2$— group is optionally replaced by an —NR— group (in which R represents a hydrogen atom, a linear or branched ($C_1$–$C_6$) alkyl group or a benzyl group), $R_4$ represents a hydroxyl group, a linear or branched ($C_1$–$C_6$) alkoxy group, a phenoxy group (substituted or otherwise with one or more halogen atoms, linear or branched ($C_1$–$C_6$) alkyl, linear or branched ($C_1$–$C_6$) alkoxy or trihalomethyl groups) or an amino group (substituted or otherwise with one or two linear or branched ($C_1$–$C_6$) alkyl groups), their isomers as well as their addition salts with a pharmaceutically acceptable base.

Among the pharmaceutically acceptable bases, there may be mentioned with no limitation being implied sodium hydroxide, potassium hydroxide, tert-butylamine, diethylamine, ethylenediamine, and the like.

The invention also extends to a process for the preparation of the compounds of formula (I) wherein there is used as starting material a compound of formula (II):

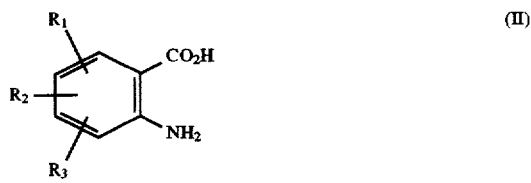

(II)

in which $R_1$, $R_2$ and $R_3$ have the same meaning as in the formula (I), which is reduced depending on the nature of the substituents $R_2$, $R_3$ and $R_4$, either in an aprotic medium in the presence of lithium aluminum hydride, aluminum hydride, diborane or borane complexes, or in an acidic protic medium when sodium cyanoborohydride is used, to give an alcohol of formula (III):

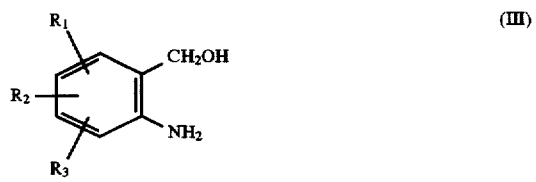

(III)

in which $R_1$, $R_2$ and $R_3$ have the same meaning as in the formula (I), which is oxidized with the aid of a metal oxide in an inert solvent, an alkali metal hydrohalide in a protic solvent or an acid chloride in dimethyl sulfoxide, to give the aldehyde of formula (IV):

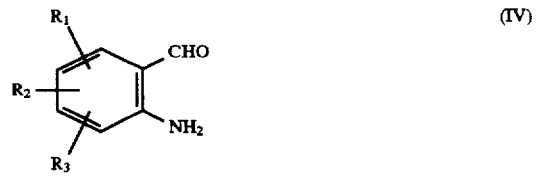

(IV)

in which $R_1$, $R_2$ and $R_3$ have the same meaning as in the formula (I), which is:

* either condensed with an alkyl malonate of formula (V), in a protic medium, in the presence of an alkali metal alcoholate, a tertiary amine or an alkali metal hydroxide according to the process described by A. Cordi et al. (Biorg. Med. Chem., 1995, 2, 129–141):

(V)

in which alk represents a linear or branched ($C_1$–$C_6$) alkyl group, to give an ester of formula (VI):

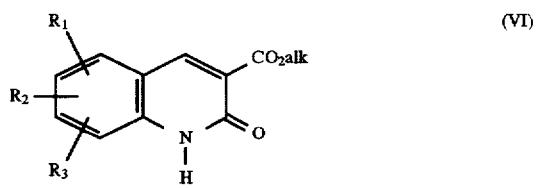

(VI)

in which $R_1$, $R_2$, $R_3$ and alk have the same meaning as above, which is converted to the corresponding acid of formula (VII):

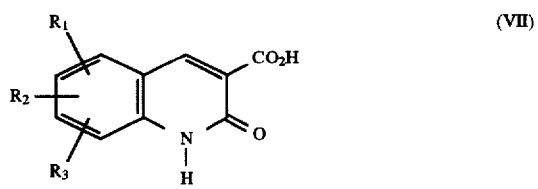

(VII)

in which $R_1$, $R_2$ and $R_3$ have the same meaning as in the formula (I), which is reacted in the presence of bromine in pyridine to give the compound of formula (VIII):

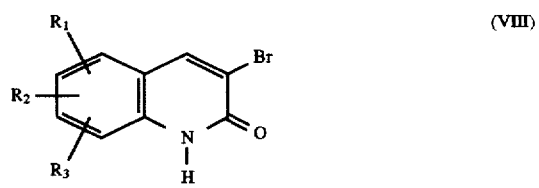

(VIII)

in which $R_1$, $R_2$ and $R_3$ have the same meaning as in the formula (I), which is reacted with a compound of formula (IX) according to the process described by P. Desos et al. (J. Med. Chem., 1996, 39, 197–206):

R'SH (IX)

in which R' represents a linear or branched ($C_1$–$C_6$) alkyl group or a —$CH_2CO_2$alk group (in which alk has the same meaning as above), to give the compound of formula (X):

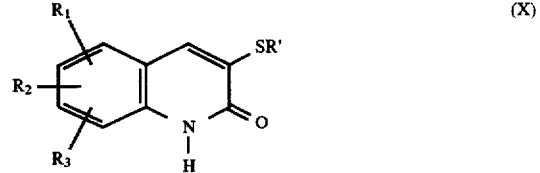

(X)

in which $R_1$, $R_2$, $R_3$ and R' have the same meaning as in the formula (I), which is subjected to oxidation in the presence of nitric acid in concentrated sulfuric acid, to give the sulfonic acid of formula (I) which may be optionally converted to the corresponding ester,

* or condensed with a compound of formula (XI) in a protic medium in the presence of an alkali metal alcoholate, a tertiary amine or an alkali metal hydroxide:

(XI)

in which $R'_4$ represents a linear or branched ($C_1$–$C_6$) alkoxy group or an optionally substituted phenoxy group, which is converted:

after an optional treatment in acidic medium, to the compound of formula (I/a), a specific case of the compounds of formula (1):

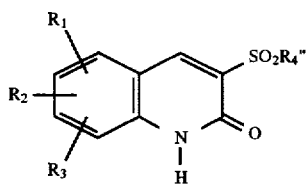

(I/a)

in which $R_1$, $R_2$ and $R_3$ are as defined above and $R''_4$ represents a hydroxyl group, a linear or branched ($C_1$–$C_6$) alkoxy group or an optionally substituted phenoxy group, which compound of formula (I/a) is optionally converted, when $R''_4$ represents a hydroxyl group, to the corresponding sulfonyl chloride, and then by the action of ammonia or an amine, to the compound of formula (I/b), a specific case of the compounds of formula (I):

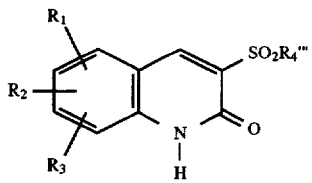

(I/b)

in which $R_1$, $R_2$, $R_3$ have the same meaning as in the formula (I) and $R'''_4$ represents an optionally substituted amino group, which compound of formula (I/a) or (I/b),

- when $R_1$ and/or $R_2$ and/or $R_3$ represent a hydrogen atom, may be subjected to electrophilic substitutions, according to conventional techniques of substitution of aromatic rings leading to a compound of formula (I) which is mono-, di- or trisubstituted on the benzene ring of the quinolinone,
- when $R_1$ and/or $R_2$ and/or $R_3$ represent a nitro group, may be subjected to hydrogenation to give the corresponding amino derivative which can itself, if desired, be converted to the corresponding cyano derivative,
- may, where appropriate, be purified according to a conventional purification technique,
- whose isomers, where appropriate, are separated according to a conventional separation technique,
- is converted, if desired, to its addition salts with a pharmaceutically acceptable base.

The compounds of formula (I) possess very advantageous pharmacological properties since they prevent the activation of the AMPA-type glutamatergic receptors. Their efficacy may be studied by means of electrophysiological techniques in vitro and especially by means of the measurement of the currents induced by the glutamatergic agonists in the oocyte of Xenopus.

Xenopus oocytes are injected with 50 ng of poly($A^+$) mRNA isolated from rat cerebral cortex and incubated for 2 to 3 days at 18° C. so as to allow the protein expression thereof. The inflow of currents induced by the EAAs are measured in a medium of composition: NaCl (82.5 mM), KCl (2.5 mM), $CaCl_2$ (1 mM), $MgCl_2$ (1 mM), $NaH_2PO_4$ (1 mM), HEPES (5 mM), pH 7.4 by the 2 electrode Voltage-clamp method (voltage=–60 mV). To measure the currents induced by NMDA and glycine, $MgCl_2$ is absent from the medium and $CaCl_2$ is supplied at the concentration of 2 mM. The EAA agonists inducing the currents are used at the following concentrations: kainate: 100 µM ; AMPA: 30 µM; glycine/NMDA: 3/30 µM. The product studied is applied 30 seconds before and during the application of the agonist.

Under these conditions, the derivatives of the present invention are capable of inhibiting the fonctional activation of the current induced by AMPA. Furthermore, their advantage lies in the fact that they exert this inhibition selectively and preferentially. Their interaction with the NMDA receptor is observed only at higher concentrations, which makes them free of all the side effects described for the NMDA antagonists (psychotomimetic, amnesic and neurotoxic effects).

Thus, the compound of Example 2 is 40 times more selective for the AMPA receptor, and this inhibition is observed at a low concentration:

AMPA: IC50=0.2 µM

NMDA: IC50=8 µM.

The subject of the present invention is also the pharmaceutical compositions containing, as active ingredient, at least one compound of formula (I), alone or in combination with one or more nontoxic inert excipients or vehicles.

Among the pharmaceutical compositions according to the invention, there may be mentioned more particularly those which are suitable for oral, parenteral or nasal administration, plain or sugar-coated tablets, sublingual tablets, gelatin capsules, lozenges, suppositories, creams, ointments, skin gels and the like.

The useful dosage varies according to the age and weight of the patient, the nature and seriousness of the condition as well as the route of administration. This may be oral, nasal, rectal or parenteral. In general, the unit dosage varies between 1 and 1000 mg for a treatment with 1 to 3 doses per 24 hours.

The following examples illustrate the invention and do not limit it in any manner. The starting materials used are materials which are known or prepared according to known procedures.

EXAMPLE 1

7-Nitro-2-(1H)-quinolinone-3-sulfonic acid 1.00 g (3.24 mmol) of 3-[(carbethoxymethyl)thio]-7-nitro-2-(1H)-quinolinone (prepared according to the procedure described by P. Desos et al. (J. Med. Chem., 1996, 39, 197–206) is dissolved in 1 ml of 96% sulfuric acid and this solution is cooled on an ice bath. 1 ml of 86% nitric acid is added dropwise. At the end of the addition, the reaction medium is allowed to return to room temperature and the stirring is continued for 4 hours (precipitation in the reaction medium). The reaction medium is again cooled to 5°–10° C. and some ice is added thereto. After stirring for 10 minutes, the precipitate is filtered, rinsed with some water and then with ether. The solid is dried under vacuum and is then solubilized in isopropanol under reflux. Some chestnut-colored insolubles are filtered while hot and the filtrate is diluted with ether until a slight cloudiness appears. The product crystallizes at room temperature and is recovered by filtration.

Melting point:>300° C.

| | Elemental microanalysis: | | | |
|---|---|---|---|---|
| | C % | H % | N % | S % |
| calculated | 40.00 | 2.24 | 10.37 | 11.87 |
| found | 39.67 | 2.29 | 10.20 | 12.28 |

EXAMPLE 2

6,7-Dinitro-2-(1H)-quinolinone-3-sulfonic acid

The compound of Example 1 (790 mg, 2.79 mmol) is dissolved in 1 ml of 96% sulfuric acid and 1 ml of 86% nitric acid is added dropwise. The reaction medium is heated at 120° C. for 5 hours. It is allowed to return to room temperature and some ice is added (the product is soluble in water). The precipitate is filtered and rinsed with a minimum of cold water and then with acetonitrile. The solid is then stirred for 12 hours in acetonitrile and is recovered by filtration.

Melting point:>300° C.

| Elemental microanalysis: | | | | |
|---|---|---|---|---|
| | C % | H % | N % | S % |
| calculated | 34.29 | 1.60 | 13.33 | 10.17 |
| found | 34.06 | 1.76 | 12.86 | 10.86 |

EXAMPLE 3

6,7-Dichloro-2-(1H)-quinolinone-3-sulfonic acid, sodium salt

A suspension containing 2.00 g (10.5 mmol) of 4,5-dichloro-2-aminobenzaldehyde (prepared according to the procedure described by A. Cordi et al., Bioorg. Med. Chem., 1995, 2, 129–141), 4.12 g (21 mmol) of ethoxysulfonylacetic acid ethyl ester (prepared according to the procedure described by M. Bordeau et al., Bull. Soc. Chim. Fr., 1986, 3, 413–417 and J. I. Trujillo et al., Tetrahedron Lett., 1993, 46, 7355–7358), 4 ml (21 mmol) of 5.25M sodium methanolate in methanol and 25 ml of anhydrous methanol, is stirred for 72 hours at room temperature. The methanol is evaporated under vacuum and the reaction medium is neutralized by adding dropwise 1N hydrochloric acid. The precipitate is filtered and taken up in 10 ml of dimethylformamide at high temperature. The mixture is allowed to return to room temperature and the white solid is filtered.

Melting point:>300° C.

| Elemental microanalysis: | | | | | |
|---|---|---|---|---|---|
| | C % | H % | N % | Cl % | S % |
| calculated | 34.20 | 1.28 | 4.43 | 22.43 | 10.14 |
| found | 33.83 | 1.37 | 4.44 | 21.88 | 9.91 |

The compounds of the following examples are prepared according to the procedure described in Example 1 from the corresponding starting materials:

EXAMPLE 4

6-(1H-Imidazol-1-yl)-7-trifluoromethyl-2-(1H)-quinolinone-3-sulfonic acid

EXAMPLE 5

6-(1H-Imidazol-1-yl)-7-nitro-2-(1H)-quinolinone-3-sulfonic acid

EXAMPLE 6

7-Chloro-6-(1H-imidazol-1-yl)-2-(1H)-quinolinone-3-sulfonic acid

EXAMPLE 7

6-(Pyrrol-1-yl)-7-trifluoromethyl-2-(1H)-quinolinone-3-sulfonic acid

EXAMPLE 8

7-Nitro-6-(pyrrol-1-yl)-2-(1H)-quinolinone-3-sulfonic acid

EXAMPLE 9

7-Chloro-6-(pyrrol-1-yl)-2-(1H)-quinolinone-3-sulfonic acid

EXAMPLE 10

7-Cyano-6-(pyrrol-1-yl)-2-(1H)-quinolinone-3-sulfonic acid

EXAMPLE 11

2-Methyl-5-chloro-8-oxo-1,2,3,4,7,8-hexahydro-[2,7]phenanthroline -9-sulfonic acid

EXAMPLE 12

2-Methyl-5-nitro-8-oxo-1,2,3,4,7,8-hexahydro-[2,7] phenanthroline -9-sulfonic acid

EXAMPLE 13

2-Methyl-5-trifluoromethyl-8-oxo-1,2,3,4,7,8-hexahydro-[2,7]phenanthroline-9-sulfonic acid

EXAMPLE 14

7-Methyl-2-oxo-2,6,7,8-tetrahydro-1H-pyrrolo[3,4-g]quinoline-3-sulfonic acid

EXAMPLE 15

2-Methyl-4-chloro-7-oxo-2,3,6,7-tetrahydro-1H-pyrrolo[3,4-f]quinoline-8-sulfonic acid

EXAMPLE 16

2-Methyl-4-nitro-7-oxo-2,3,6,7-tetrahydro-1H-pyrrolo[3,4-f]quinoline-8-sulfonic acid

EXAMPLE 17

2-Methyl-4-trifluoromethyl-7-oxo-2,3,6,7-tetrahydro-1H-pyrrolo[3,4-f]quinoline-8-sulfonic acid Pharmacological Study of the Derivatives of the Invention

EXAMPLE 18
Anti-convulsant activity in vivo

The excessive liberation of glutamate is very widely involved in the onset of convulsive attacks in man. Experimentally, the same phenomenon may be reproduced by the injection of glutamatergic agonists in rats and in mice. Likewise, in the DBA2 mice, glutamate-dependent convulsive attacks may be triggered by subjecting the animals to a sound stimulus of high frequency (14 kHz, 103 dB). The anticonvulsion effects are objectivated by the capacity to prevent convulsions arrival and the death which follows.

Administered by the i.p. route 30 minutes before imposing the sound stimulus, the compounds of the invention exert anticonvulsant effects and these effects are proportional to the administered doses.

Thus, the compound of Example 1 strongly protects the animals (ED50=26.9 mg/kg) and at the dose of 50 mg/kg, the mortality is inhibited by more than 80% in the treated animals.

EXAMPLE 19
Antineurodegenerative activity in vivo

The occlusion of the sylvian artery (or middle cerebral artery MCA) is at the origin of about 70% of cases of cerebral vascular accidents in man. This type of cerebral ischemia may be reproduced very precisely in rats by intracerebral ligature of the MCA. This definitive occlusion causes, within 24 hours, the formation of a striatocortical infarct of identical location to that observed in a clinical situation. The infarct is perfectly delimited and is therefore histologically measurable. This infarct is of the edematous type. It changes within the following 3 days into a definitive necrotic infarct. The excessive liberation of glutamate is a major pathological feature for the genesis of the cerebral infarct. An antiischemic neuroprotective compound should prevent the formation of this infarct at 24 hours and on its necrotic maturation at 96 hours.

The compounds of the invention are compounds with a potent antiischemic effect, even during post-ischemic delayed treatment (treatment by the i.v. route 1 hour after the arterial occlusion). Thus, at the dose of 20 mg/kg i.v., the compounds of Examples 1 and 2 significantly reduce the cortical edematous infarct volume by 45 and 27% respectively. This is a major activity since it also prevents necrotic maturation. Thus, when a 3-day follow-up treatment (10 mg/kg i.p. twice per day) is carried out after the initial i.v. injection (20 mg/kg), the compound of Example 1decreases the volume of the terminal infarct by 44%.

EXAMPLE 20
Pharmaceutical composition

Preparation formula for 1000 tablets containing 10 mg doses

| | |
|---|---|
| Compound of Example 1 | 10 g |
| Hydroxypropylcellulose | 2 g |
| Wheat starch | 10 g |
| Lactose | 100 g |
| Magnesium stearate | 3 g |
| Talc | 3 g |

We claim:

1. A compound select from those of formula (I):

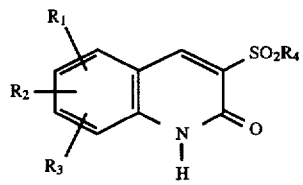

in which:

$R_1$, $R_2$, $R_3$, which are identical or different, represent hydrogen, halogen, linear or branched ($C_1$–$C_6$) alkyl (substituted or not with one or more halogen), nitro, cyano, aminosulfonyl, imidazolyl (substituted or not with one or more linear or branched ($C_1$–$C_6$) alkyl or linear or branched amino($C_1$–$C_6$) alkyl), or pyrrolyl (substituted or not with one or more linear or branched ($C_1$–$C_6$) alkyl or linear or branched amino($C_1$–$C_6$) alkyl), $R_4$ represents hydroxyl, linear or branched ($C_1$–$C_6$) alkoxy, phenoxy (substituted or not with one or more halogen, linear or branched ($C_1$–$C_6$) alkyl, linear or branched ($C_1$–$C_6$) alkoxy, or trihalomethyl), or amino (substituted or not with one or two linear or branched ($C_1$–$C_6$) alkyl), their optical isomers as well as their addition salts with a pharmaceutically-acceptable base provided that at least one of $R_1$, $R_2$ and $R_3$ is other than hydrogen.

2. A compound of claim 1, wherein at least one of the groups $R_1$, $R_2$ and $R_3$ represents nitro.

3. A compound of claim 1, wherein $R_4$ represents hydroxyl.

4. A compound of in claim 1, which is 7-nitro-2-(1H)-quinolinone-3-sulfonic acid.

5. A compound of in claim 1, which is 6,7-dinitro-2-(1H)-quinolinone-3-sulfonic acid.

6. A compound of claim 1, which is 6,7-dichloro-2-(1H)-quinolinone-3-sulfonic acid, sodium salt.

7. A method for treating a living body afflicted with a condition, selected from the group consisting of cerebral vascular accident, cerebral or spinal trauma, epilepsy, ischemia, and convulsions comprising the step of administering to the living body an amount of a compound of claim 1 which is effective for alleviation of said condition.

8. A pharmaceutical composition useful in inhibiting EAA hyperactivation of neurotransmission pathways comprising as active principle an effective amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 5,776,949
DATED : July 7, 1998
INVENTOR(S) : A. Cordi, P. Desos, J. Lepagnol, P. Morain, P. Lestage It is certified that error appears in the above-indentified patent and that said Letters Patent is hereby corrected as shown below:

Column 2, line 20: "The compounds of the   " should start a new paragraph.

Column 10, line 8(approx.): The word "select" should read -- selected --.

Column 10, line 46: Delete the word "in".

Column 10, line 48: Delete the word "in".

Signed and Sealed this

Sixth Day of October, 1998

Attest:

*Attesting Officer*

BRUCE LEHMAN

*Commissioner of Patents and Trademarks*